United States Patent
Llewellyn

(10) Patent No.: US 7,199,112 B2
(45) Date of Patent: Apr. 3, 2007

(54) USE OF PHOSPHOLIPID ARACHIDONIC ACIDS FOR INCREASING MUSCLE MASS IN HUMANS

(76) Inventor: William Llewellyn, 5500 Military Trail #22-308, Jupiter, FL (US) 33458

( * ) Notice: Subject to any disclaimer, the term of this patent is extended or adjusted under 35 U.S.C. 154(b) by 0 days.

(21) Appl. No.: 11/501,431

(22) Filed: Aug. 9, 2006

(65) Prior Publication Data

US 2007/0036849 A1 Feb. 15, 2007

Related U.S. Application Data

(60) Provisional application No. 60/707,057, filed on Aug. 10, 2005.

(51) Int. Cl.
*A61K 31/685* (2006.01)
*A61K 31/66* (2006.01)
(52) U.S. Cl. ........................................ 514/78; 514/114
(58) Field of Classification Search ................... None
See application file for complete search history.

(56) References Cited

U.S. PATENT DOCUMENTS 5,853,747 A * 12/1998 Ponroy ........................ 424/439
5,965,413 A * 10/1999 Sakai et al. .................. 435/106

* cited by examiner

*Primary Examiner*—Raymond J. Henley, III
(74) *Attorney, Agent, or Firm*—Holland & Knight LLP

(57) ABSTRACT

This invention discloses a method of increasing muscle mass comprising administering phospholipid arachidonic acid to a human in need thereof.

8 Claims, No Drawings

USE OF PHOSPHOLIPID ARACHIDONIC ACIDS FOR INCREASING MUSCLE MASS IN HUMANS

CROSS REFERENCE TO RELATED APPLICATIONS

This application claims priority benefit from provisional application Ser. No. 60/707,057 filed on Aug. 10, 2005.

BACKGROUND OF THE INVENTION

Maintaining healthy levels of muscle mass and body fat can play an important role in sustaining overall good health, with benefits such as increased basal metabolic rate, better disposal of dietary fats, easier maintenance of lower body fat levels, increased immune system health, and an increase in one's overall vitality and sense of well-being. A number of conditions exist which make it difficult to maintain a normal healthy level of lean muscle mass, including HIV (human immunodeficiency virus), andropause or hypogonadism (subnormal androgen levels), obesity, infection, trauma, burns, and spinal cord injury. Some individuals also fail to gain or to maintain normal lean body mass and body fat without definite pathophysiologic reasons. Many treatments promote the buildup of muscle tissue. Fewer treatments, however, offer the ability to improve and increase lean muscle mass (i.e. insure that skeletal muscle tissue gain is not accompanied by body fat gain, or is even accompanied by a lowering of body fat levels).

Skeletal muscle mass is increased or maintained in the body through a number of distinct mechanisms. Such mechanisms play a role in the regulation of either skeletal muscle protein synthesis or breakdown. Collectively, they control the total amount of accrued protein present in the muscle cell. The actions of androgens are tied to the regulation of skeletal muscle mass. It is well documented that raising the level of androgenic hormones in the body can increase skeletal muscle mass. A number of methods have similarly been developed to increase the level of androgenic hormones in the body, which ultimately can be used to offer the benefits of increased skeletal muscle mass in humans. The use of androgenic hormones in general, however, is thought to be relevant to the development of undesirable side effects such as gynecomastia, water retention (edema), fat buildup, unfavorable alterations in cholesterol levels (increased heart disease risk), and increased blood pressure. If an individual seeking to increase skeletal muscle mass is not in need of androgen replacement, then the methods regarding the use of androgens may be less than ideal.

U.S. Pat. No. 6,841,573 ("the '573 patent") relates to a method of using arachidonic acid for increasing PGF2-alpha, protein synthesis rates, and skeletal muscle mass. The '573 patent provides a solution for an individual in need of increasing skeletal muscle mass, because PGF2-alpha is non-steroidal, and can increase protein synthesis and muscle mass without the potential undesirable side effects associated with altering sex steroid levels with androgen hormones. Due to the high cost of manufacture and supplementation, however, arachidonic acid may not be an ideal solution for everyone. Therefore, it is an object of this invention to provide alternative compositions and methods for improving lean muscle mass, or the ration of lean to fat mass, in humans.

BRIEF SUMMARY OF THE INVENTION

The present invention measurably improves the anabolic effect of arachidonic acid with the use of an attached secondary messenger molecule that will work synergistically with arachidonic acid. According to the invention this problem is solved by the use of phosphatidylcholine arachidonic acid, lysophosphatidylcholine arachidonic acid, and/or phosphatidylserine arachidonic acid. The secondary messengers phosphatidylcholine, phosphatidylserine, and lysophosphatidylcholine are not provided as free molecules, but as part of single intact molecules of phosphatidylcholine arachidonic acid, lysophosphatidylcholine arachidonic acid, or phosphatidylserine arachidonic acid. Upon enzymatic disassociation in the body, phosphatidylcholine, lysophosphatidylcholine, or phosphatidylserine and arachidonic acid will work synergistically to increase skeletal muscle protein synthesis and growth rates, as well as to slow, stall, or reverse lipogenesis in humans. In addition, the ratio of lean muscle mass to fat mass is increased in the body.

DETAILED DESCRIPTION OF THE INVENTION

Arachidonic acid is a naturally occurring polyunsaturated fat, belonging to the Omega-6 family of fatty acids. It is considered an essential dietary fatty acid (EFA). It is obtained in small amounts in the average human diet, coming from various plant and animal sources including beef and eggs. Arachidonic acid has furthermore been identified as a vital precursor to numerous hormones in the body including prostaglandins, prostacyclin 12 (PGI2), leukotrienes, and thromboxanes. Arachidonic acid itself plays a vital role in skeletal muscle protein synthesis. This dietary nutrient is stored in the phospholipid layer of skeletal muscle cells, and is released during intense exercise. This release regulates the local production of prostaglandins, which regulate skeletal muscle protein synthesis and breakdown rates, and the normal anabolic response to resistance exercise. Arachidonic acid also plays a role in the differentiation of adipose cells, and can inhibiting or slowing this effect depending on the metabolic context (Metabolism. 1998 April;47(4):461–6). This makes arachidonic acid not only vital to skeletal muscle growth, but may make it integral to the disposition of body fat in humans as well. Arachidonic acid exists in nature most widely as a free acid or triglyceride; however, it is also found as a phospholipid. Phospholipid-bound arachidonic acid is the subject of this invention. In the phospholipid arachidonic acid molecule, two fatty acids (arachidonic acids) are attached to a phospholipid, forming a di-arachidonic acid phospholipid. Such phospholipids include, but are not limited to, phosphatidylcholine, phosphatidylserine, lysophosphatidylcholine, phosphatidylethanolamine, phosphatidylinositol and sphingomyelin.

Phosphatidylcholine is a naturally occurring phospholipid and a major constituent of cell membranes. It is an important dietary nutrient, used by the body for the repair and normal functioning of cell membranes. Phosphatidylcholine is also the major dietary provider of choline, an essential nutrient and precursor in the synthesis of acetylcholine, a neurotransmitter in the body. Phosphatidylcholine is also involved in the hepatic removal of low-density lipoproteins, and may help regulate cholesterol balance. With regard to potential mechanisms for increasing lean skeletal muscle growth, phosphatidylcholine has also been shown to exert an IGF-1 response in certain cell studies (Cell Physiol Biochem. 2005; 15(5):211–24). This inventor set out to show that phosphatidylcholine arachidonic acid acts synergistically as a phospholipid bound to arachidonic acid. Arachidonic acid is known to exert an IGF-1-type effect by supporting the phosphoinositide 3-kinase (P13K) pathway (Biochem Biophys Res Commun. 2003 Oct. 3;309(4):755–61). The P13K pathway is a pathway in which IGF-1 mediates its cellular effects (J Biol. Chem. 2005 Jan. 28;280(4):2737–44. Epub 2004 Nov. 17). In-vivo, the phosphatidylcholine and arachidonic acid, bound together, could provide a greatly amplified anabolic effect compared to free arachidonic acid, and would be better for increasing lean muscle mass.

Phosphatidylserine is a naturally occurring phospholipid, and a structural component of the biological cell membranes of animals. Intravenous infusion of phosphatidylserine significantly suppresses the normal adrenocorticotropin (ACTH) and cortisol response to stressful exercise (Neuroendocrinology. 1990 September;52(3):243–8). Although their effects on resistance exercise and muscle growth were not examined, cortisol is widely understood to be a strong regulator of skeletal muscle growth. Cortisol increases the release of amino acids from skeletal muscle cells. Cortisol is a catabolic hormone, and does not increase skeletal muscle growth. By suppressing the cortisol response to physical exercise, normally categorized by a marked increase in production, phosphatidylserine may increase the overall level of retained protein by shifting the balance of protein synthesis and breakdown in favor of protein synthesis.

Lysophosphatidylcholine is a naturally occurring phospholipid. Studies have shown that lysophosphatidylcholine increases intestinal transport of certain nutrients (for example, J. Nutr. 131:2921–2927, November 2001). Nutrient availability is a vital and regulating factor in the growth of skeletal muscle, as various nutrients provide the building blocks of skeletal tissues. Lysophosphatidylcholine can be used as a sole dietary supplement for increasing the digestion rate of foods. Lysophosphatidylcholine ("LPC") arachidonic acid might also share such effect on digestion and intestinal permeability, and perhaps more importantly, that the increase in intestinal transport of vital nutrients due to LPC would actually have an enhancing effect on anabolism, thereby providing greater effectiveness when compared to therapy with free arachidonic acid.

The oral bioavailability of fatty acids when bound to phospholipids like phosphatidylcholine, phosphatidylserine, lysophosphatidylcholine, phosphatidylethanolamine, phosphatidylinositol and sphingomyelin, makes clear the suitability of such modified molecules for oral fatty acid supplementation (Cell. Mol. Biol. 50(7), 815–831). The individual properties of arachidonic acid, phosphatidylcholine, phosphatidylserine, and lysophosphatidylcholine play important roles in regulating lean muscle mass growth and fat disposition in humans. In addition, fatty acids can disassociate from phospholipids.

It is the object of this invention to increase lean skeletal muscle mass by the oral administration of phosphatidylcholine arachidonic acid, lysophosphatidylcholine arachidonic acid, and/or phosphatidylserine arachidonic acid. Another object of the present invention is to increase the ratio of lean muscle mass to body fat mass. A clinical study was therefore undertaken by the inventor. Specifically, it was shown that phosphatidylcholine arachidonic acid, lysophosphatidylcholine arachidonic acid, or phosphatidylserine arachidonic acid would act as effective in-vivo peroral agents for increasing lean skeletal muscle mass in humans. Such agents also slow, stall, or reverse lipogenesis in humans. Furthermore, these agents may be used to increase the ration of lean muscle mass to body fat mass.

Administering phosphatidylethanolamine arachidonic acid, phosphatidylinositol arachidonic acid, and sphingomyelin arachidonic acid to a person may also be used to increase muscle mass.

To date, there have no investigations into the effects of oral phosphatidylcholine arachidonic acid, lysophosphatidylcholine arachidonic acid, or phosphatidylserine arachidonic acid on lean muscle mass in humans or animals. Furthermore, there have no studies directed to the effects of phosphatidylcholine arachidonic acid, lysophosphatidylcholine arachidonic acid, or phosphatidylserine arachidonic acid on body fat disposition in humans. Lastly, there have been no determinations made as to whether there is any synergy between free arachidonic acid and free phosphatidylcholine, lysophosphatidylcholine, or phosphatidylserine and lean muscle mass or body fat retention in humans.

The present invention provides methods of using pharmaceutical compositions of the inventive compounds. Such pharmaceutical compositions may be for administration by injection, or by oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release); by sublingual, anal, vaginal, or by surgical implantation, e.g., embedded under the splenic capsule, brain, or in the cornea. The treatment may consist of a single dose or a plurality of doses over a period of time. In general, comprehended by the invention are pharmaceutical compositions comprising effective amounts of a compound of the invention together with pharmaceutically acceptable diluents, preservatives, solubilizers, emulsifiers, adjuvants and/or carriers. Such compositions include diluents of various buffer content (e.g., Tris-HCl, acetate, phosphate), pH and ionic strength; additives such as detergents and solubilizing agents (e.g., Tween 80, Polysorbate 90), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc. or into liposomes. Hyaluronic acid may also be used, and this may have the effect of promoting sustained duration in the circulation. The pharmaceutical compositions optionally may include still other pharmaceutically acceptable liquid, semisolid, or solid diluents that serve as pharmaceutical vehicles, excipients, or media, including but are not limited to, polyoxyethylene sorbitan monolaurate, magnesium stearate, methyl- and propylhydroxybenzoate, starches, sucrose, dextrose, gum acacia, calcium phosphate, mineral oil, cocoa butter, and oil of theobroma. Such compositions may influence the physical state, stability, rate of in vivo release, and rate of in vivo clearance of the present proteins and derivatives. See, e.g., Remington's Pharmaceutical Sciences, 18th Ed. (1990, Mack Publishing Co., Easton, Pa. 18042) pages 1435–1712 which are herein incorporated by reference. The compositions may be prepared in liquid form, or may be in dried powder, such as lyophilized form. Implantable sustained release formulations are also contemplated, as are transdermal formulations.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets or pellets, and powder that may or may not be dissolved in a liquid. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the phospholipid arachidonic acid is illustrated by Marshall, K., Modern Pharmaceutics, Edited by G. S. Banker and C. T. Rhodes Chapter 10, 1979, herein incorporated by reference. In general, the formulation will include the inventive compound, and inert ingredients which allow for protection against the stomach environment, and release of the biologically active material in the intestine. The oral dosage forms contemplated herein can be administered at any time of the day or night. These oral dosage forms may be administered or taken one or more times per day or night. It is preferable that the oral dosage forms be administered or taken between 1 and 10 times per day or night. It is still more preferable that the oral dosage forms be administered or taken between 1 and 5 times per day or night. It is still more preferable that the oral dosage forms be administered or taken between 2 and 3 times per day or night.

Also specifically contemplated are oral dosage forms of the above inventive compounds. If necessary, the compounds may be chemically modified so that oral delivery is efficacious. Generally, the chemical modification contemplated is the attachment of at least one moiety to the compound molecule itself, where said moiety permits (a) inhibition of proteolysis; and (b) uptake into the blood stream from the stomach or intestine. Also desired is the increase in overall stability of the compound and increase in circulation time in the body. Examples of such moieties include: Polyethylene glycol, copolymers of ethylene glycol and propylene glycol, carboxymethyl cellulose, dextran, polyvinyl alcohol, polyvinyl pyrrolidone and polyproline (Abuchowski and Davis, Soluble Polymer-Enzyme Adducts, Enzymes as Drugs, Hocenberg and Roberts, eds., Wiley-Interscience, New York, N.Y., (1981), pp 367–383; Newmark, et al., J. Appl. Biochem. 4:185–189 (1982)). Other polymers that could be used are poly-1,3-dioxolane and poly-1,3,6-tioxocane. Preferred for pharmaceutical usage, as indicated above, are polyethylene glycol moieties.

For the oral delivery dosage forms, it is also possible to use a salt of a modified aliphatic amino acid, such as sodium N-(8-[2-hydroxybenzoyl]amino) caprylate (SNAC), as a carrier to enhance absorption of the compounds of this invention. The clinical efficacy of a heparin formulation using SNAC has been demonstrated in a Phase II trial conducted by Emisphere Technologies. See U.S. Pat. No. 5,792,451, "Oral drug delivery composition and methods".

The phospholipid arachidonic acid can be included in the formulation as fine multiparticulates in the form of granules or pellets of particle size about 1 mm. The formulation of the material for capsule administration could also be as a powder, lightly compressed plugs or even as tablets. The compound could be prepared by compression.

Colorants and flavoring agents may all be included. For example, the protein (or derivative) may be formulated (such as by liposome or microsphere encapsulation) and then further contained within an edible product, such as a refrigerated beverage containing colorants and flavoring agents.

One may dilute or increase the volume of the phospholipid arachidonic acid with an inert material. These diluents could include carbohydrates, especially mannitol, .alpha.-lactose, anhydrous lactose, cellulose, sucrose, modified dextrans and starch. Certain inorganic salts may also be used as fillers including calcium triphosphate, magnesium carbonate and sodium chloride. Some commercially available diluents are Fast-Flo, Emdex, STA-Rx 1500, Emcompress and Avicell.

Disintegrants may be included in the formulation of the phospholipid arachidonic acid into a solid dosage form. Materials used as disintegrants include but are not limited to starch including the commercial disintegrant based on starch, Explotab. Sodium starch glycolate, Amberlite, sodium carboxymethylcellulose, ultramylopectin, sodium alginate, gelatin, orange peel, acid carboxymethyl cellulose, natural sponge and bentonite may all be used. Another form of the disintegrants is the insoluble cationic exchange resins. Powdered gums may be used as disintegrants and as binders and these can include powdered gums such as agar, Karaya or tragacanth. Alginic acid and its sodium salt are also useful as disintegrants.

Binders may be used to hold the phospholipid arachidonic acid agent together to form a hard tablet and include materials from natural products such as acacia, tragacanth, starch and gelatin. Others include methyl cellulose (MC), ethyl cellulose (EC) and carboxymethyl cellulose (CMC). Polyvinyl pyrrolidone (PVP) and hydroxypropylmethyl cellulose (HPMC) could both be used in alcoholic solutions to granulate the contemplated compounds.

Controlled release formulation may be desirable. The contemplated compounds could be incorporated into an inert matrix which permits release by either diffusion or leaching mechanisms e.g., gums. Slowly degenerating matrices may also be incorporated into the formulation, e.g., alginates, polysaccharides. Another form of a controlled release of the contemplated compounds is by a method, wherein the compound is enclosed in a semipermeable membrane which allows water to enter and push the compounds out through a single small opening due to osmotic effects. Some enteric coatings also have a delayed release effect.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto The following non-limiting example and data illustrates various aspects and features relating the methods and compositions of the present invention. While the utility of this invention may be illustrated through the use of several methods, it will be understood by those skilled in the art that comparable results are obtainable with various other methods, as are commensurate with the scope of this invention.

EXAMPLE I

Effective Dosages

During the course of developing this invention, an effective oral daily dosage of phosphatidylcholine arachidonic acid to increase lean muscle mass was determined to be between 50 mg to 4,000 mg. An effective oral daily dosage of phosphatidylserine arachidonic acid to increase lean muscle mass was determined to be between 50 mg to 4,000 mg. An effective oral daily dosage of lysophosphatidylcholine arachidonic acid to increase lean muscle mass was determined to be between 50 mg to 4,000 mg. Due to the rapidity in which the discussed compounds are metabolized in the body, the total daily dosage can be further subdivided for more sustained blood hormone concentrations, with 2–3 applications per day being most preferred.

I claim:

1. A method for increasing muscle mass comprising administering to a human in need thereof an effective amount of phospholipid arachidonic acid.

2. The method of claim 1, wherein the effective amount of phospholipid arachidonic acid is between about 50 mg and 4,000 mg.

3. The method of claim 2, wherein the effective amount of phospholipid arachidonic acid is administered between 1 and 10 times per day.

4. The method of claim 1, wherein the effective amount of phospholipid arachidonic acid is administered by a route selected from the group consisting of oral, intravenous, intramuscular, and intrapulmonary.

5. The method of claim 4, wherein the route is oral.

6. The method of claim 1, wherein the effective amount of phospholipid arachidonic acid is administered in a pharmaceutical composition.

7. The method of claim 6, wherein the pharmaceutical composition comprises agents selected from the group consisting of diluents, preservatives, solubilizers, emulsifiers, and carriers.

8. The method of claim 1, wherein the phospholipid arachidonic acid is selected from the group consisting of phosphatidylcholine arachidonic acid, lysophosphatidylcholine arachidonic acid, and phosphatidylserine arachidonic acid.

* * * * *